(12) United States Patent
Perelman et al.

(10) Patent No.: US 6,922,583 B1
(45) Date of Patent: *Jul. 26, 2005

(54) METHOD FOR MEASURING TISSUE MORPHOLOGY

(75) Inventors: Lev T. Perelman, Brookline, MA (US); Vadim Backman, Cambridge, MA (US); Michael S. Feld, Newton, MA (US); George Zonios, Ioannina (GR); Irving Itzkan, Boston, MA (US); Ramasamy Manoharan, Cambrigde, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/545,992

(22) Filed: Apr. 10, 2000

Related U.S. Application Data

(63) Continuation of application No. PCT/US98/21450, filed on Oct. 9, 1998, which is a continuation-in-part of application No. 08/948,734, filed on Oct. 10, 1997, now Pat. No. 6,091,984.

(51) Int. Cl.[7] .................................................. A61B 6/00
(52) U.S. Cl. ...................................................... 600/476
(58) Field of Search ................................ 600/476, 478, 600/310; 356/432, 345, 346, 357

(56) References Cited

U.S. PATENT DOCUMENTS

| | | | |
|---|---|---|---|
| 3,675,768 A | 7/1972 | Legorreta-Sanchez | 209/4 |
| 4,281,931 A | 8/1981 | Chikama | 356/372 |
| 4,336,809 A | 6/1982 | Clark | 128/665 |
| 4,515,165 A | 5/1985 | Carroll | 128/664 |
| 4,655,225 A | 4/1987 | Dähne et al. | 128/633 |
| 4,718,417 A | 1/1988 | Kittrell et al. | 128/303.1 |
| 4,829,184 A | 5/1989 | Nelson et al. | 250/358.1 |
| 4,930,516 A | 6/1990 | Alfano et al. | 128/665 |
| 4,948,974 A | 8/1990 | Nelson et al. | 250/358.1 |
| 5,106,387 A | 4/1992 | Kittrell et al. | 606/15 |
| 5,168,162 A | 12/1992 | Oong et al. | 250/339 |
| 5,243,615 A | 9/1993 | Ortiz et al. | 372/34 |
| 5,284,137 A | 2/1994 | Kessler et al. | 128/633 |
| 5,303,026 A | 4/1994 | Strobl et al. | 356/318 |
| 5,309,907 A | 5/1994 | Fang et al. | 128/633 |
| 5,313,264 A | 5/1994 | Ivarsson et al. | 356/73 |
| 5,317,156 A | 5/1994 | Cooper et al. | 250/345 |
| 5,345,306 A | 9/1994 | Ichimura et al. | 356/346 |
| 5,369,496 A | 11/1994 | Alfano et al. | 356/446 |
| 5,386,827 A | 2/1995 | Chance et al. | 128/633 |

(Continued)

FOREIGN PATENT DOCUMENTS

| | | |
|---|---|---|
| WO | 92/14399 | 9/1992 |
| WO | 96/28084 | 9/1996 |
| WO | 96/29926 | 10/1996 |

OTHER PUBLICATIONS

Newton, R.G., *Scattering Theory of Waves and Particles*, Second Ed. Chapter 2, "Spherically Symmetric Scatters", pp. 30–53 Chapter 3, "Limiting Cases and Approximations", pp. 54–78.

Primary Examiner—Marvin M. Lateef
Assistant Examiner—Eleni Mantis Mercader
(74) Attorney, Agent, or Firm—Weingarten, Schurgin, Gagnebin & Lebovici LLP

(57) ABSTRACT

The present invention relates to systems and methods for measuring one or more physical characteristics of material such as tissue using optical radiation. The system can use light that is scattered by a tissue layer to determine, for example, the size of nuclei in the tissue layer to aid in the characterization of the tissue. These methods can include the use of fiber optic devices to deliver and collect light from a tissue region of interest to diagnose, for example, whether the tissue is normal or precancerous.

34 Claims, 14 Drawing Sheets

U.S. PATENT DOCUMENTS

| | | | |
|---|---|---|---|
| 5,398,685 A | 3/1995 | Wilk et al. | 128/653.1 |
| 5,402,778 A | 4/1995 | Chance | 128/633 |
| 5,419,321 A | 5/1995 | Evans | 128/633 |
| 5,421,337 A | 6/1995 | Richards-Kortum et al. | 128/665 |
| 5,452,723 A | 9/1995 | Wu et al. | 128/664 |
| 5,460,177 A | 10/1995 | Purdy et al. | 128/633 |
| 5,491,344 A | 2/1996 | Kenny et al. | 250/461.1 |
| 5,560,356 A | 10/1996 | Peyman | 128/633 |
| 5,582,168 A | 12/1996 | Samuels et al. | 128/633 |
| 5,582,169 A | 12/1996 | Oda et al. | 128/633 |
| 5,596,987 A | 1/1997 | Chance | 128/633 |
| 5,596,992 A | 1/1997 | Haaland et al. | 128/664 |
| 5,625,458 A | 4/1997 | Alfano et al. | 356/446 |
| 5,630,423 A | 5/1997 | Wang et al. | 128/664 |
| 5,636,633 A | 6/1997 | Messerschmidt et al. | 128/633 |
| 5,640,247 A | 6/1997 | Tsuchiya et al. | 356/446 |
| 5,713,364 A | 2/1998 | DeBaryshe et al. | 128/664 |
| 5,733,739 A | 3/1998 | Zakim et al. | 435/29 |
| 5,813,987 A | 9/1998 | Modell et al. | 600/473 |
| 5,919,140 A | 7/1999 | Perelman et al. | 600/476 |
| 5,931,789 A | 8/1999 | Alfano et al. | 600/473 |
| 5,994,690 A | 11/1999 | Kulkarni et al. | 250/216 |
| 6,002,480 A * | 12/1999 | Izatt et al. | 356/345 |
| 6,091,984 A | 7/2000 | Perelman et al. | 600/476 |

* cited by examiner

METHOD FOR MEASURING TISSUE MORPHOLOGY

RELATED APPLICATIONS

This is a continuation application of International Application No. PCT/US98/21450 filed on Oct. 9, 1998 which is a continuation-in-part of U.S. Ser. No. 08/948,734 filed on Oct. 10, 1997, now U.S. Pat. No. 6,091,984, the entire contents of the above applications being incorporated herein by reference.

GOVERNMENT SUPPORT

The invention was supported, in whole or in part, by a Grants No. P41RR02594 and CA53717 from the National Institutes For Health. The Government has certain rights in the invention.

BACKGROUND OF THE INVENTION

Methods for diagnosis of cancer at an early stage are essential for cancer prevention and therapy. Many types of cancers grow from epithelial tissues, which cover inner and outer surfaces of the human body. Many of these, for example cancer in gastrointestinal tract, progress through the stage of dysplasia. Dysplasia can be defined as neoplastic tissue which is not malignant yet, but is considered to be a precursor of malignancy. If diagnosed at this stage, most tumors are curable. In the case of gastrointestinal tumors, current methods of diagnosis are based on endoscopy. However, dysplastic tissue is frequently not endoscopically apparent. Thus, detection of dysplasia in the gastrointestinal tract and other sites often relies on sporadic sampling for this "invisible" malignant precursor. However, sporadic biopsies have a high probability of missing dysplastic changes. In some cases the biopsy procedure is impossible.

Efforts toward a substitution for standard biopsies have been made in order to provide accurate diagnosis of cancerous tissue in different organs in vivo and in real time. For this purpose, optical techniques that are non-invasive do not require tissue removal and can be performed in-vivo. Such methods provide information at the microscopic level and can thus provide for the search for very small sites which are likely to be missed by standard biopsies. While most human organs can be diagnosed by means of optical techniques, they are particularly applicable to the tissues in human body lumene, since they are easily accessible by optical probes, which can be inserted into one of the channels of a conventional endoscopic tube.

SUMMARY OF THE INVENTION

The present invention relates to the use of light to determine physical characteristics of a structured layer of material, and in particular certain qualitative information regarding the morphology of tissue structures using scattered light. Both backscattered and transillumination methods can be used, depending upon the thickness of the material and the size and distribution of the structure being measured. Examples of properties of materials that can be measured include surface roughness, parasity, cytometer measurements, or any material in which changes in the refractive index of a material correspond to changes in structures. This type of scattering spectroscopy can be differentiated from absorption spectroscopy which is unable to quantitatively measure particle morphology.

Despite extensive investigations, no reliable optical technique to diagnose dysplasia in-vivo is known. One of the difficulties resides in the fact that dysplastic changes are limited to the uppermost epithelial layer, which can be as thin as 20 $\mu$m, a one cell layer that is nearly transparent to optical radiation.

Tissue in the gastrointestinal tract, for example (other hollow organs share the same features also), is covered by a layer of cells called epithelium (from 20 $\mu$m to 300 $\mu$m thick depending on the part of the tract) supported by relatively acellular and highly vascular loose connective tissue, lamina propria, which can be up to 500 $\mu$m in thickness and contains a network of collagen and elastic fibers, and variety of white blood cell types. Beneath the lamina propria there is a muscular layer, muscularis mucosae, (up to 400 $\mu$m thick) and another layer of moderately dense connective tissue called submucosa (400–600 $\mu$m thick) containing many small blood vessels and abundant collagen and elastic fibers. The overall thickness of those layers is about 1 mm. Since a characteristic penetration depth of optical radiation into biological tissue does not usually exceed 1 mm, for a preferred embodiment it is sufficient to limit measurements of tissue by those layers.

Adenocarcinoma of the esophagus arises in metaplastic columnar epithelial cells in the esophagus, termed "Barrett's esophagus", which is a complication of long-standing gastrointestinal reflux. In this condition, the distal squamous epithelium is replaced by columnar epithelium consisting of a one cell layer which resembles that found in the intestines. Barrett's esophagus is frequently associated with dysplasia which later can progress to cancer. Trials of endoscopic surveillance of patients with Barrett's esophagus have not resulted in a reduction of esophageal cancer mortality. The most likely explanation is that dysplasia occurring in the esophagus cannot be seen with standard endoscopic imaging and sporadic biopsy sampling is necessary. This procedure can sample only about 0.3% of the tissue at risk. Thus, there is tremendous potential for sampling error.

The application of optical techniques to diagnose dysplasia in Barrett's esophagus is limited by the fact that the primary alterations in the tissue occur in the epithelium which is one cell thick (~20–30 $\mu$m) while fluorescence or reflectance spectra are mostly formed in deeper tissue layers. One of the most prominent features of a dysplastic epithelium is the presence of enlarged, hyperchromatic, and crowded nuclei. In fact, these changes in nuclei size and spatial distribution are the main markers used by a pathologist to diagnose a tissue specimen as being dysplastic. No significant changes in other tissue layers is observed. Unfortunately, epithelium does not contain strong absorbers or fluorophores, and the thickness of the epithelium is relatively small and thus negligible. These make epithelium diagnosis in Barrett's esophagus to be a difficult problem.

Diffuse reflectance spectroscopy can provide quantitative biochemical and morphological information for the analysis of biological tissue epithelium and the detection of precancerous lesions. Diffuse reflectance spectra were collected from adenomatous colon polyps (cancer precursors) and normal colonic mucosa of patients undergoing colonoscopy. The data were analyzed using an analytical light diffusion system, which was measured on a physical tissue model composed of polystyrene beads and hemoglobin. Four parameters were obtained: hemoglobin concentration, hemoglobin oxygen saturation, effective scatterer density, and effective scatterer size. Normal and adenomatous tissue sites exhibited differences in hemoglobin concentration and effective scatterer size. Thus, diffuse reflectance can be used to obtain tissue biochemical and morphological information in vivo.

A preferred embodiment of the present invention relates to a system of measuring a fine structure component in backscattered light from mucosal tissue which is periodic in wavelength. This structure is ordinarily masked by a diffusive background, which must be removed to render it observable. The origin of this component is due to light which is Mie-scattered by surface epithelial cell nuclei. By analyzing the amplitude and frequency of the periodic structure, the density and size distribution of these nuclei can be extracted. These quantities are important indicators of neoplastic precancerous changes in biological tissue, and the technique can thus provide a useful tool for observing such changes in patients undergoing endoscopy.

The light that is incident on the thin layer at the tissue surface is not completely randomized. In this thin region the details of the elastic scattering process can be preserved. Mucosal tissues, which line the hollow organs of the body, generally consist of a thin surface layer of epithelial cells supported by underlying, relatively acellular connective tissue. In healthy tissues the epithelium often consists of a single, well-organized layer of cells with an endface diameter of about 10–20 $\mu$m and a height of about 25 $\mu$m. In cancerous and pre-cancerous (dysplastic) epithelium cells proliferate, the cellular layer often thickens and becomes more tightly packed, and the cell nuclei enlarge and appear darker (hyperchromatic) when stained. This may indicate increased nucleic acid density, hence increased refractive index.

A preferred embodiment of the invention utilizes a broadband light source to illuminate the region of interest in the tissue with optical radiation in the range between 350 and 700 nm. A fiber optic probe can be used to deliver and/or collect radiation from the tissue. The system can be used during endoscopy of a patient to optically survey a body lumen within the patient and thereby eliminate the need for removal of tissue for biopsy, or alternatively, can be used to aid in locating tissue suitable for biopsy.

Backscattered light is preferably collected over a small collection angle of between 2° and 12°, preferably in the range between 3° and 8°. When using an optical fiber system to collect the scattered light fibers having a numerical aperture between 0.05 and 0.22, and preferably between 0.07 and 0.1 can be used. Collection angles within this range reduce the level of background light without loss of the periodic component in the returning light.

Figure 1:
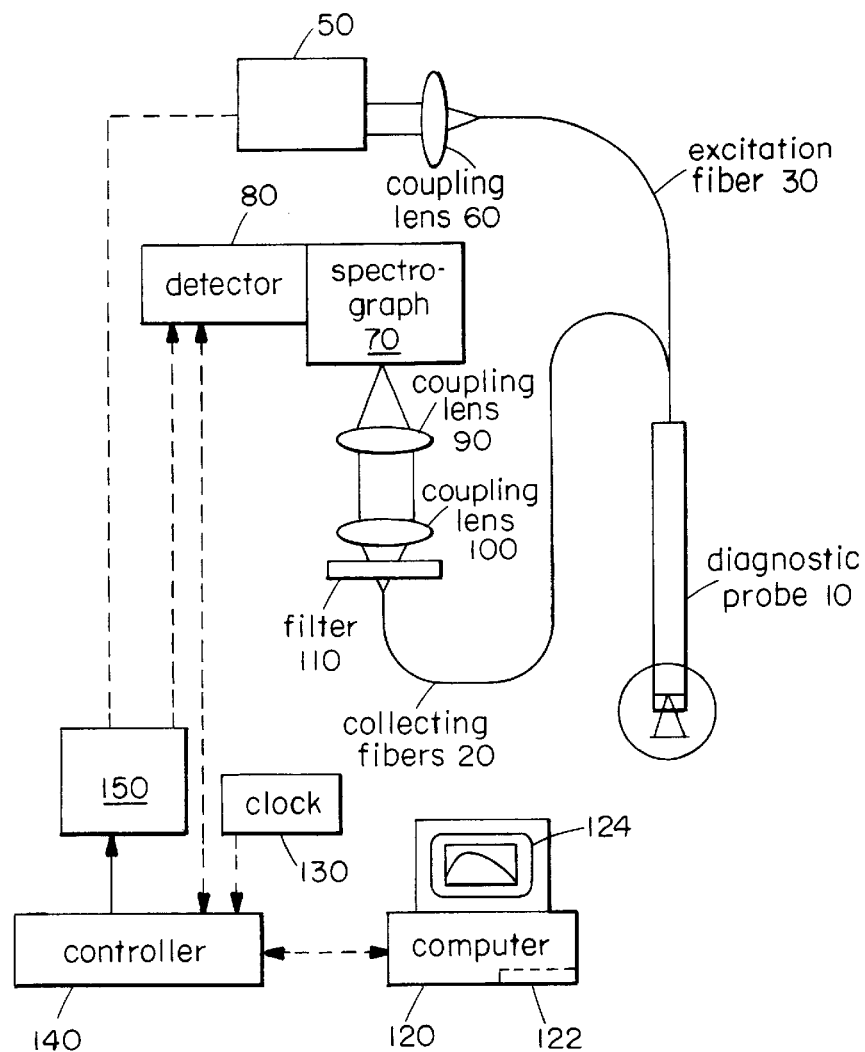
FIG. 1 is a schematic diagram of a fiber optic probe in accordance with the invention.

The foregoing and other objects, features and advantages of the invention will be apparent from the following more particular description of preferred embodiments thereof, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A preferred embodiment of the invention involves the use of a fiber optic system to deliver and collect light from a region of interest to measure one or more physical characteristics of a surface layer. Such a system is illustrated in FIG. 1. This system can include a light source 50 such as a broadband source, a fiber optic device for delivery and/or collection of light from the tissue, a detector system 80 that detects the scattered light from the tissue, a computer 120 having a memory 122 that analyzes and stores the detected spectra, and a display 124 that displays the results of the measurement. A lens 60 can be used to couple light from the source 50 into the excitation fiber 30 of the probe 10. A filter 110 and lens system 90, 100 can be used to efficiently couple collected light to a spectrograph 70. A controller 140 connected to the data processing system 120 can be connected to a clock and a pulser 150 that controls the light source 50.

Figure 2:
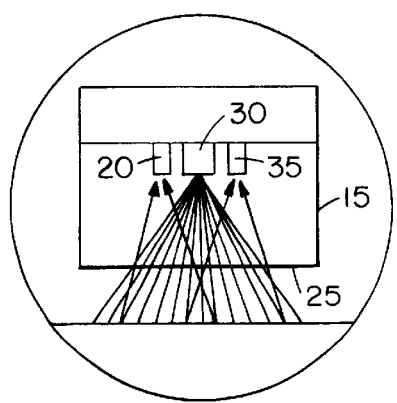
FIG. 2 is an enlarged view of the distal end of an endoscope in accordance with the invention.

The distal end 15 of the probe 10 is illustrated in FIG. 2 where the central excitation fiber 30 is surrounded by six peripheral collection fiber 20. The distal end of the device can be enclosed in an optical shield 25 such as that described in U.S. Pat. No. 5,199,431, the entire contents of which is incorporated herein by reference. Other endoscopic devices can be used such as an optical needle as described in the above referenced patent or as described in U.S. Pat. No. 5,280,788, the entire contents of which is also incorporated herein by reference.

The collection fibers 20 preferably have a numerical aperture in the range of 0.05 to 0.22 in order to provide a desired collection angle from the material being measured. This aids in reducing background that is removed from scattering spectrum without loss of the periodic component.

The collection fibers can also be replaced or supplemented by a distally mounted imaging sensor 35 such as a charged coupled device or CMOS imager. The sensor has a pixellated structure that is sensitive to the different colors contained in the scattering spectrum being recorded. Further details regarding the use of a distally mounted sensor can be found in U.S. Ser. No. 08/745,509 filed on Nov. 12, 1996, the entire contents of which is incorporated herein by reference.

The backscattered light collected with this system can be analyzed to determine certain physical characteristics of epithelial tissue. The relationship between the collected light and the physical characteristics to be determined using this light can be described as follows.

Epithelial nuclei can be represented as spheroidal Mie scatterers with a refractive index higher than that of the surrounding cytoplasm. Normal nuclei have a characteristic diameter $1=4-7$ $\mu$m. In contrast, dysplastic nuclei can be as large as 20 $\mu$m in size, occupying almost the entire cell volume. Thus, in the visible range, the wavelength $\lambda<<1$, and the component of light scattered by the nuclei will exhibit a periodicity with wavelength, the details of which are determined by the nuclear size distribution. The Van de Hulst approximation can be used to describe the optical scattering cross section of the nuclei:

$$\sigma_s(\lambda, l) = \frac{1}{2}\pi l^2 \left\{ 1 - \frac{\sin(2\delta/\lambda)}{\delta/\lambda} + \left(\frac{\sin(\delta/\lambda)}{\delta/\lambda}\right)^2 \right\}, \quad (1)$$

where $\delta=\pi l n_c(n-1)$, with $n_c$ the refractive index of cytoplasm and n the refractive index of the nuclei relative to that of cytoplasm.

When a beam of light is incident on an epithelial layer of tissue, a portion of this light is backscattered from the epithelial nuclei, while the remainder is transmitted to deeper tissue layers, where it undergoes multiple scattering and becomes randomized. All of the diffusive light which is not absorbed in the tissue eventually returns to the surface, passing once more through the epithelium, where it is again subject to scattering from the cell nuclei. Thus, the emerging light consists of a large diffusive background plus the component of forward scattered and backscattered light from the nuclei in the epithelial layer. For a thin slab of epithelial tissue containing nuclei with size distribution N(l) (number of nuclei per unit area (mm$^2$) and per unit interval of nuclear diameter ($\mu$m)), the approximate solution of the transport equation for the reflectance R($\lambda$) collected by an optical probe with acceptance solid angle $\Omega_c$ is given by the following expression:

$$\frac{R(\lambda)}{\bar{R}(\lambda)} = e^{-\tau(\lambda)} + 1 - \frac{e^{-\tau(\lambda)}}{I_d(\lambda, s)\Omega_c} \langle I_i(\lambda, -s^1)p(\lambda, s, -s^1)\rangle\Omega_i + \quad (2)$$

$$\langle I_d(\lambda, s^1)p(\lambda, s, s^1)\rangle_{2\pi} \Big|\Omega_c$$

where $I_i((\lambda,s))$ is the intensity of the incident light delivered in solid angle $\Omega_i$, $I_d(\lambda,s)$ is the intensity of the light emerging from the underlying tissue, and $$\langle I(s)\rangle\Omega = \int_\Omega I(s)ds$$

for any function I(s) and solid angel $\Omega$, with s a unit vector pointing outward from the tissue surface in an arbitrary direction. The quantity $\bar{R}(\lambda)=<I_d(\lambda, s)>\Omega_c/<I_i(\lambda, s)>\Omega_c$ is the reflectance of the diffusive background. The optical distance $$\tau(\lambda) = \int_0^\infty \sigma_s(\lambda, l)N(l)dl$$

and scattering phase function $$p(\lambda, s, s^1) = \frac{1}{\tau}\int_0^\infty \rho(\lambda, l, s, s^1)\sigma_s(\lambda, l)N(l)dl$$

both depend on N(l); for a sphere, p($\lambda$,l,s,s$^1$) is determined by Mie theory. The first term in Eq. (2) describes the attenuation of the diffusive background, and the terms in brackets describe backscattering of the incident light and forward scattering of diffusive background by the epithelial cell nuclei, respectively.

For small $\Omega_c$ the forward scattering term in Eq. (2) can be expanded in $\tau(\lambda)$. Thus, $$<I_d(\lambda,s^1)p(\lambda,s,s^1)>2\pi>\Omega_c/<I_d(\lambda,s)>\Omega_c \cong f_0+f_1$$

$\tau/\tau_0$, with $$\tau_0 = \pi/2 \int_0^\infty l^2 N(l)dl.$$

It is found numerically that $f_1<<f_0$ and that $f_0$ and $f_1$ are approximately independent of wavelength in the range of interest ($\lambda_{min}=360$ to $\lambda_{max}=685$ nm). Similarly, for the backscattering term, $<(I_i(\lambda,-s^1)p(\lambda,s)>\Omega_c/<I_d(\lambda,s)>\Omega_c \cong b_0-b_1\tau/\tau_0$. Note that in the forward scattering contribution the first order term oscillates in phase with $\tau(\lambda)$, as required by the optical theorem, whereas for the backscattering contribution it is out of phase. Thus, Eq. (2) reduces to $$\frac{R(\lambda)}{\bar{R}(\lambda)} = e^{-\tau(\lambda)} + (1 - e^{-\tau(\lambda)})\left(f_0 + b_0 + (f_1 - b_1)\frac{\tau(\lambda)}{\tau_0(\lambda)}\right), \quad (3)$$

which shows that the epithelial nuclei introduce a periodic fine structure component into the reflectance with a wavelength dependence similar to that of the corresponding scattering cross section. Its periodicity is approximately proportional to nuclear diameter, and its amplitude is a function of the size and number of nuclei in the epithelial layer. These quantities can be determined by analyzing the reflectance, R($\lambda$).

As example of the effects described by Eq. (2), elastic light scattering from normal T84 tumor human colonic cell monolayers (10 and 15 sites respectively) was measured and analyzed. The cells, approximately 15 $\mu$m long, were affixed to glass slides in buffer solution and placed on top of a $BaSO_4$ diffusing (and highly reflective) plate. The $BaSO_4$ plate was used to approximate the diffuse reflectance from underlying tissue. The diameters of the normal cell nuclei generally ranged from 5 to 7 $\mu$m and those of the tumor cells from 7 to 16 $\mu$m.

An optical fiber probe was used to deliver white light from a xenon arc flashlamp to the samples and collect the return reflectance signal, as shown in FIG. 1. The probe tip, 1 mm in diameter, consisted of a central delivery fiber surrounded by six collection fibers, all of which were covered with a 1 mm thick quartz optical shield. The fibers were 200 $\mu$m core fused silica, NA=0.22 ($\Omega_i=\Omega_c=\pi NA^2$). To eliminate specular reflection, the probe was beveled at 17° to the normal. At the proximal end the collection fibers were arranged in a line and imaged onto the input slit of a spectrograph. A diode array detector recorded the reflectance spectra from 360 to 685 nm.

Figure 3A:
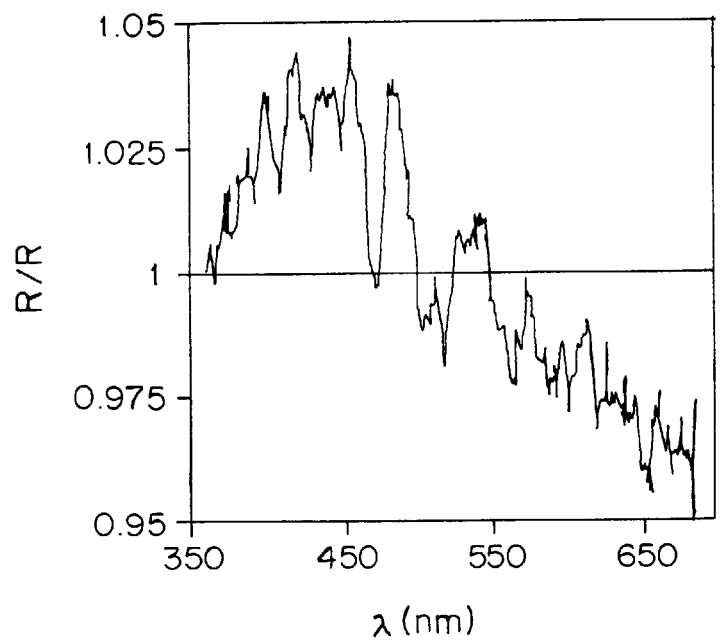
FIGS. 3A, 3B and 3C illustrate reflectance spectra from cell monolayers for normal colon cells ($\overline{R}$=0.46); T84 cells ($\overline{R}$=0.38); (c) $BaSO_4$ diffusing plate ($\overline{R}$=1.0)
Figure 3B:
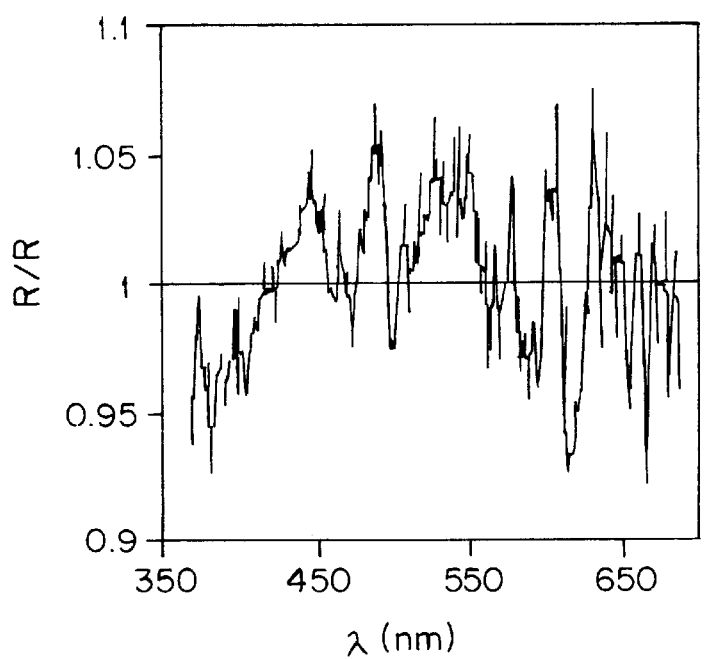
Figure 3C:
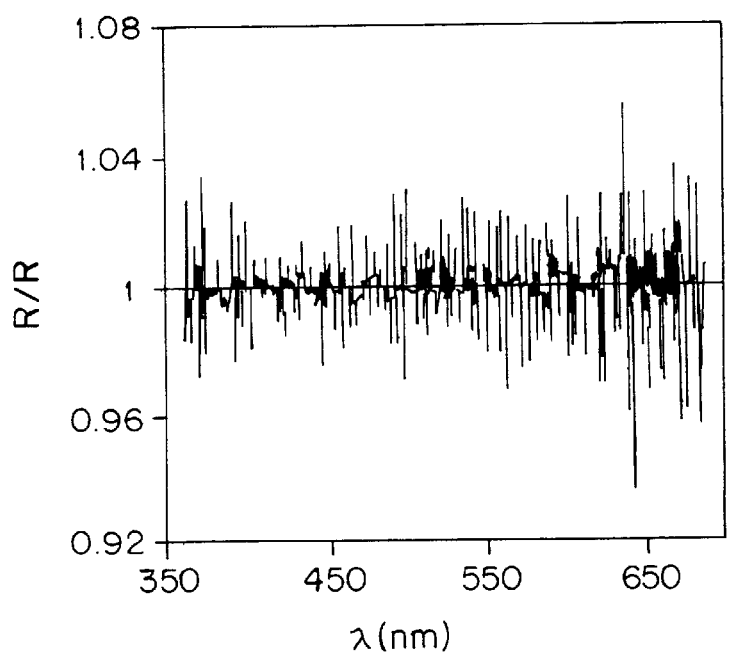

FIGS. 3A and 3B show the normalized reflectance $R(\lambda)/\overline{R}(\lambda)$ from normal and T84 tumor cell samples, respectively. Distinct spectral features are apparent. For comparison, the reflectance spectrum from the $BaSO_4$ plate by itself is also shown in FIG. 3C. This spectrum lacks structure and shows no prominent features.

To obtain information about the nuclear size distribution from the reflectance data, Eq. (3) needs to be inverted. The nuclear size distribution, N(1), can then be obtained from the Fourier transform of the periodic component of the optical distance $\tau-\tau_0 \cong (1-R(\lambda))/q$. The parameter $q=1-b_0-f_0+2(b_1-f_1)$ is associated with forward and backward scattering, and depends on the probe geometry and the angular distribution of the incident and reflected light. In this particular example $q \approx 0.15$. By introducing the effective wavenumber $k=2\Pi n_c (n-1)/\lambda - k_0$, and $k=2\pi n_c(n-1)/\lambda_{max}$, $K=2\pi n_c(n-1)<\lambda_{min}^{-1} - \lambda_{max}^{-1}>$ and we obtain, $$N(l) \cong \frac{2}{ql\pi^2} \left| \int_0^K \left( \frac{R(k)}{\overline{R}(k)} - 1 \right) e^{ikl}(k+k_0)dk \right|. \quad (4)$$

Figure 4:
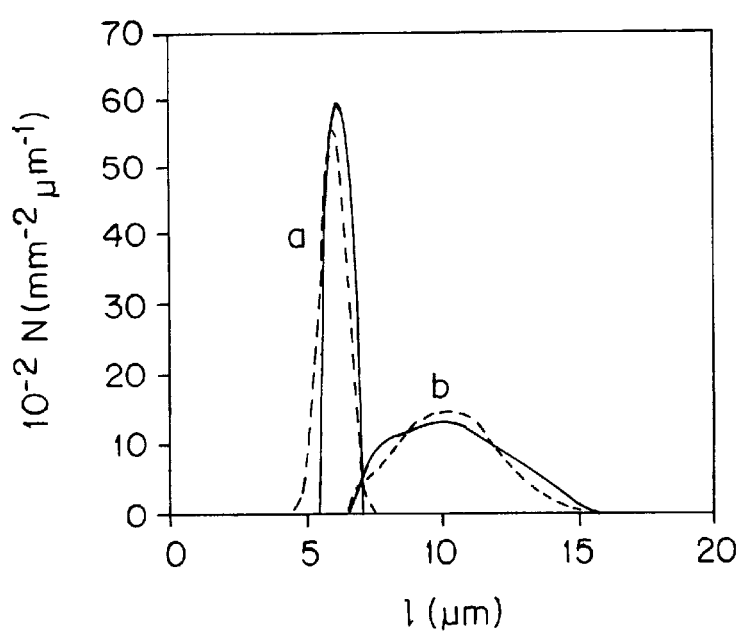
FIG. 4 illustrates nuclear size distributions from data of FIGS. 3A and 3B, respectively for normal colon cells; and T84 cells respectively. In each case, the solid line is the distribution extracted from the data, and the dashed line is the distribution measured using light microscopy.

Equation (4) was used to analyze the data. In order to remove spurious oscillations, N(1) was further processed by convolving it with a Gaussian filtering function. The solid curves in FIG. 4 show the resulting nuclear size distributions of the normal and T84 cell monolayer samples extracted from the spectra of FIGS. 3A and 3B. A nucleus-to-cytoplasm relative refractive index of n=1.06 and cytoplasm refractive index of $n_c$=1.36 were used. The dashed curves show the corresponding size distributions, measured morphometrically via light microscopy. The size distributions can be approximated by Gaussian distributions. The parameters for those are presented in Table 1. The extracted and measured distributions are in good agreement for both normal and T84 cell samples.

TABLE 1

|  | Normal Cells | | Tumor T84 Cells | |
| --- | --- | --- | --- | --- |
|  | Mean Diameter ($\mu$m) | Standard Deviation ($\mu$m) | Mean Diameter ($\mu$m) | Standard Deviation ($\mu$m) |
| Microscopy | ~6 | ~0.5 | 10.2 | 2.0 |
| Spectroscopy | 6.2 | 0.45 | 10.1 | 2.2 |

The periodic fine structure in diffuse reflectance of esophagus and colon mucosa of human subjects can be measured during gastroenterological endoscopy procedures. In the case of Barretts' esophagus, in which the epithelium consists of a thin monolayer of columnar cells similar to those used in the cell culture experiments, data were collected as in the cell culture studies. The optical fiber probe is inserted into the biopsy channel of the endoscope and brought into contact with the tissue surface. The methods described herein can also be used to measure structural properties of other GI tissue, tissues in the oral cavity, the cervix, the bladder, and skin.

Figure 5A:
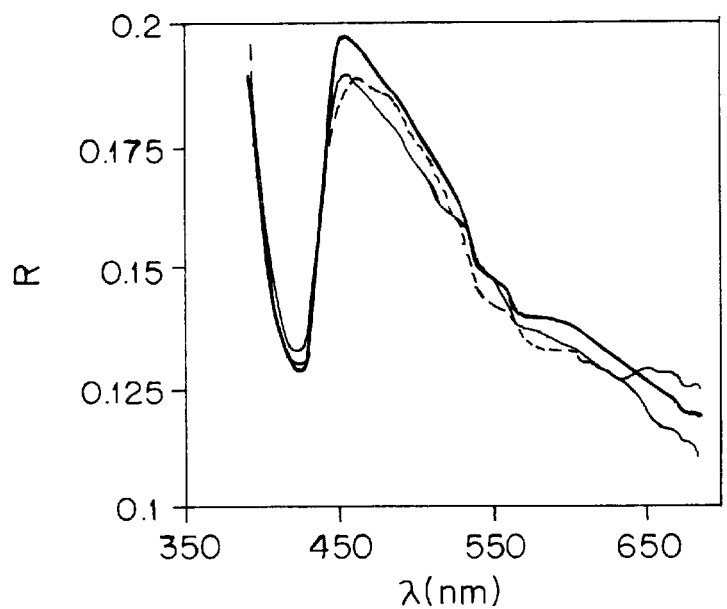
FIGS. 5A, 5B and 5C are reflectance spectra from Barretts' esophagus for diffuse reflectance from a normal site (solid line), a dysplastic site (dashed line), and the model fit (thick solid line); for corresponding fine structures; and of resulting nuclear size distributions, respectively.

The fine structure component, which is the scattering signature of the cell nuclei, is typically less then 5% of the total signal and is ordinarily masked by the background of diffusely scattered light from underlying tissue, which itself exhibits spectral features due to absorption and scattering, as shown in FIG. 5A. Its spectral features are dominated by the characteristic absorption bands of hemoglobin and collagen scattering. In order to observe the fine structure, this background must be removed. The absorption length, $\mu_a^{-1}$, ranges from 0.5 to 250 mm as the wavelength is varied, and the effective scattering length $(\mu_s')^{-1}$ ranges from 0.1 to 1 mm. Thus, both scattering and absorption have to be taken into account in subtracting or removing the background signal.

To represent the background light incident on the tissue is assumed to be exponentially attenuated, and that at any given depth, z, an amount of light proportional to the reduced scattering coefficient $\mu_s'$ is scattered back towards the surface and further exponentially attenuated. Since light attenuation depends on both scattering and absorption, the attenuation coefficient is assumed to be the sum of absorption coefficient $\mu_a$ and effective scattering coefficient $\mu_s^{(e)} = \beta\mu_s'$. The parameter $\beta$ was determined by comparison with Monte Carlo simulations and more accurate models of light transport, and was found to be $\approx 0.07$. Since light only penetrates ~1 mm into the tissue, most of the diffusely scattered return light is confined to the mucosal layer.

The tissue is thereby represented as a two layer medium and neglected diffusely reflected light from the lower layer. The following approximate expression for the diffusive light from underlying tissue impinging on the epithelial cell layer is then obtained:

$$I_d(\lambda, s) = F(s)\langle I_i(\lambda, s)\rangle_{\Omega_i} \frac{1 - \exp[-(\mu_s^{(e)} + c\mu_a)L]}{1 + c(\mu_a/\mu_s^{(e)})}, \quad (5)$$

with F(s) being a Lambertian function describing the angular dependence of light emerging from mucosal layer, L a parameter representing the thickness of the mucosal layer, and L a parameter representing the thickness of the mucosal layer, and c, the concentration of hemoglobin, which we find to be the main absorber relative to that of collagen, which is responsible for light scattering. Because both oxygenated and deoxygenated hemoglobin are present, the total hemoglobin absorption is represented as $\mu_a = (1-a)\mu_a^{(Hb)} + \alpha\mu_a^{(Hb)_2)}$ with oxygen saturation parameter $\alpha (0<\alpha<1)$.

Figure 5B:
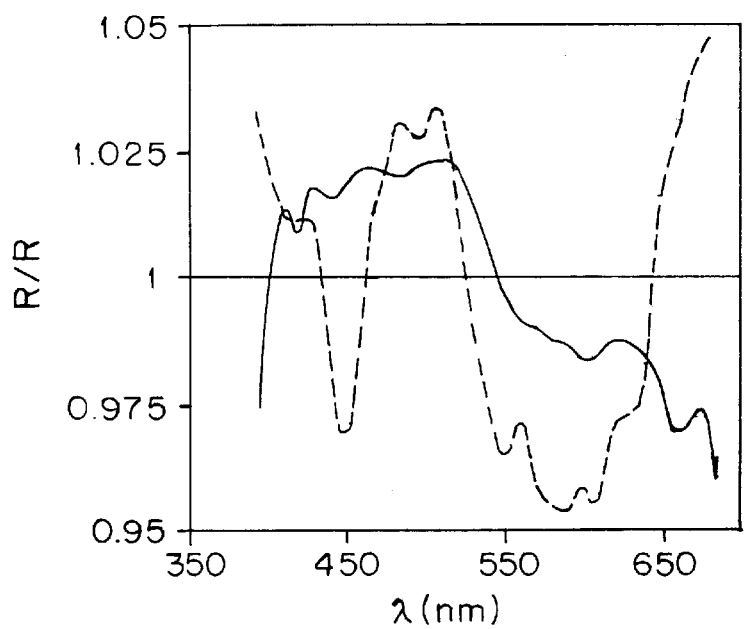
Figure 5C:
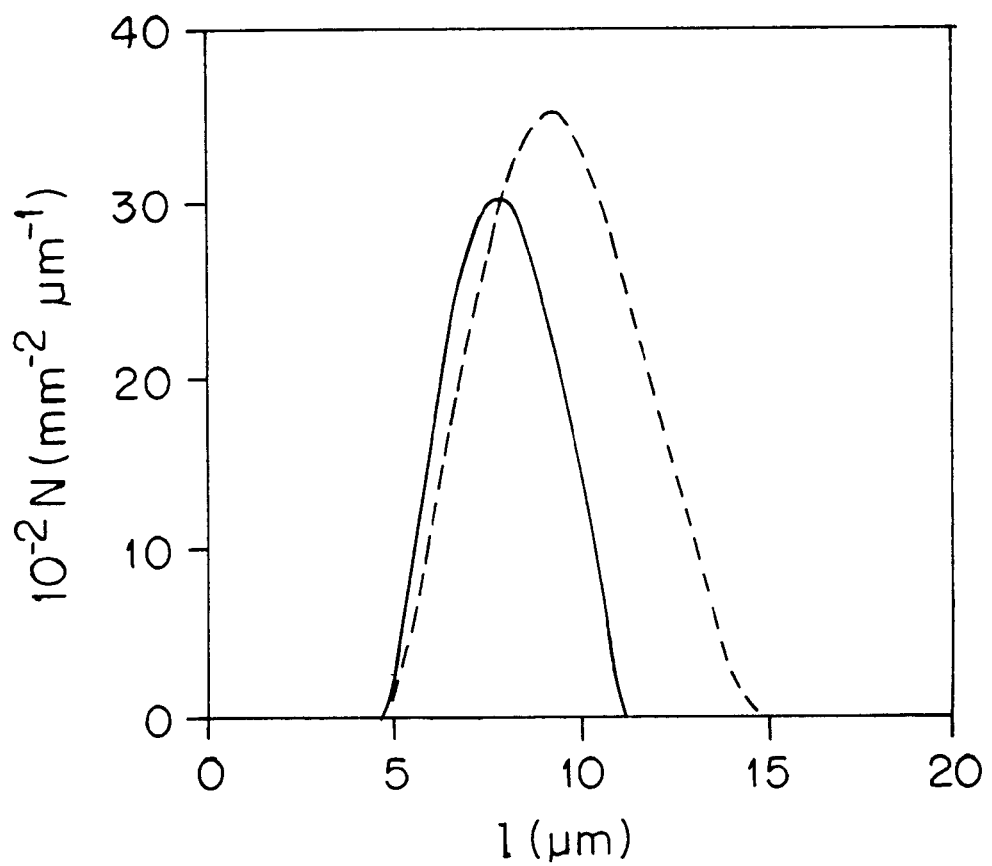

FIG. 5A shows the reflectance spectra from two Barretts' esophagus tissue sites, both independently diagnosed by standard pathological analysis to indicate (1) normal and (2) precancerous (i.e. low grade dysplasia). As can be seen, the differences in these unprocessed spectra are small. To analyze them, Eq. (5) was first fit to the broad features of the data by varying the parameters c, a and L. As seen in FIG. 5A, the resulting fits are quite accurate. After removing this diffuse background structure by calculating $R(\lambda)/\overline{R}(\lambda)$, the periodic fine structure is seen in FIG. 5B. Note that the fine structure from the dysplastic tissue site exhibits higher frequency content than that from the normal site. Equation (4) was then employed to extract the respective nuclear size distributions, yielding FIG. 5C. The difference between normal and dysplastic tissue sites is evident. The distribution of nuclei from the dysplastic site is much broader than that from the normal site and the peak diameter is shifted from ~7 µm to about ~10 µm. In addition, both the relative number of large nuclei (>10 µm) and the total number of nuclei are significantly increased.

Based on computer analysis, the uncertainty of the above method in extracting nuclear size information is estimated to be from 5% to 30%, depending on the noise level and accuracy of the model. The distributions were calculated using the same refractive index for both normal and dysplastic nuclei. This is not entirely correct, inasmuch as in stained histological sections dysplastic nuclei appear hyperchromatic, which may be indicative of an increase in refractive index. Thus, the relative number of large nuclei in the distributions measured from dysplastic sites may be slightly overestimated.

The ability to measure nuclear size distribution in vivo has valuable applications in clinical medicine. Enlarged nuclei are primary indicators of cancer, dysplasia and cell regeneration. In addition, measurement of nuclei of different size can provide information about the presence of particular cells, and can thus serve, for example, as an indicator of inflammatory response of biological tissue. This suggests that different morphology/pathology in the mucosal layer gives rise to distinct patterns of nuclear distributions.

Figure 6:
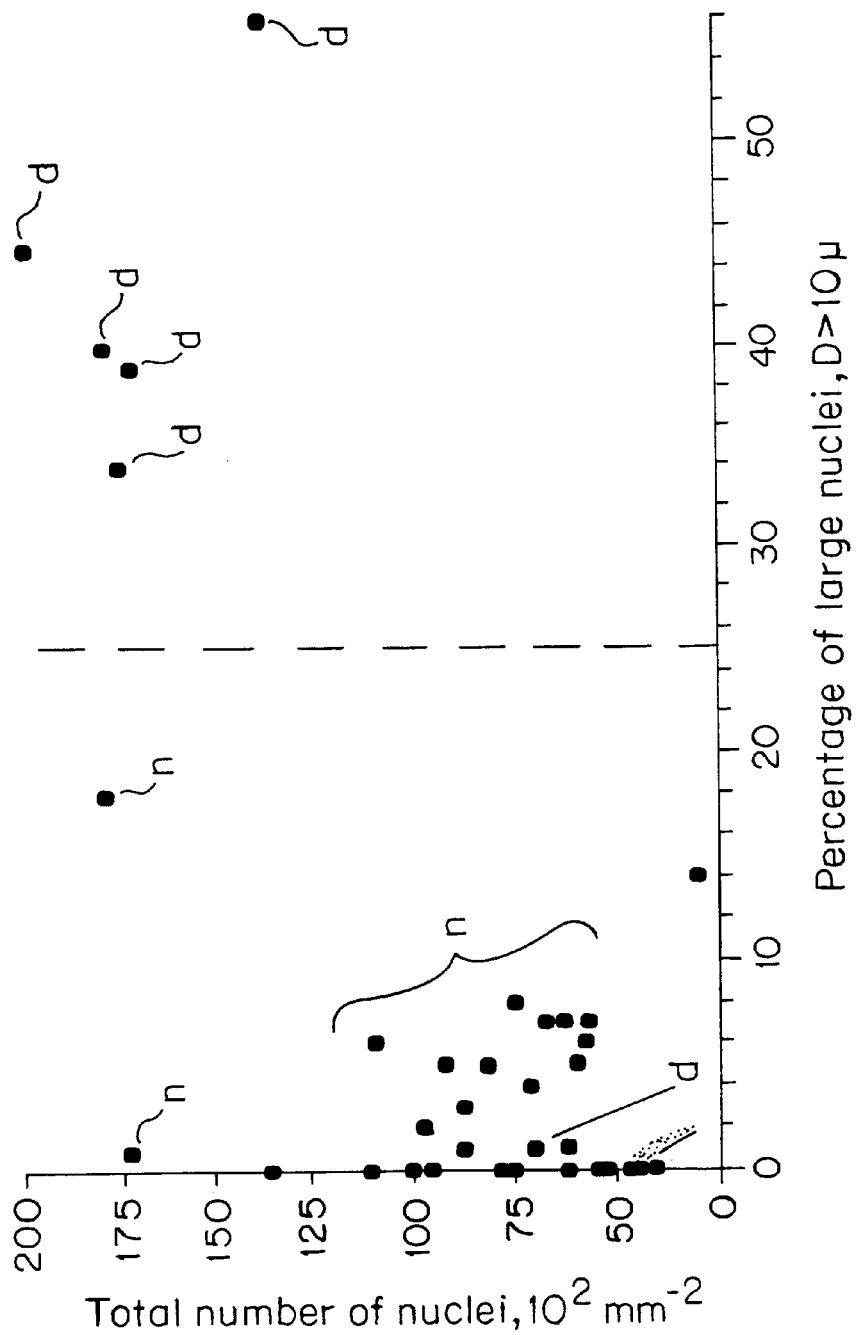
FIG. 6 graphically illustrates a comparison of samples analyzed by standard pathology and the optical methods in accordance with the invention.

The physical characteristics that have been found to be useful to differentiate between Barrett's non-dysplastic and dysplastic epithelium were the total number of nuclei and the percentage of large nuclei (1>10 µm). A comparison of pathological analysis of samples with the optical analysis thereof provided the plot (total number of nuclei vs. percentage of nuclei with a diameter large that 10 µm) in FIG. 6. From those 50 sites, the cumulative sensitivity and specificity, for this analysis were 83% and 100% respectively. The study had a positive predictive value is 100%. The points indicated by n's were either normal or inflamed and those indicated by d's were displastic. A percentage in the range of 20–30% was found to be an accurate diagnostic for this type, with 25% being used in this particular example.

Figure 7:
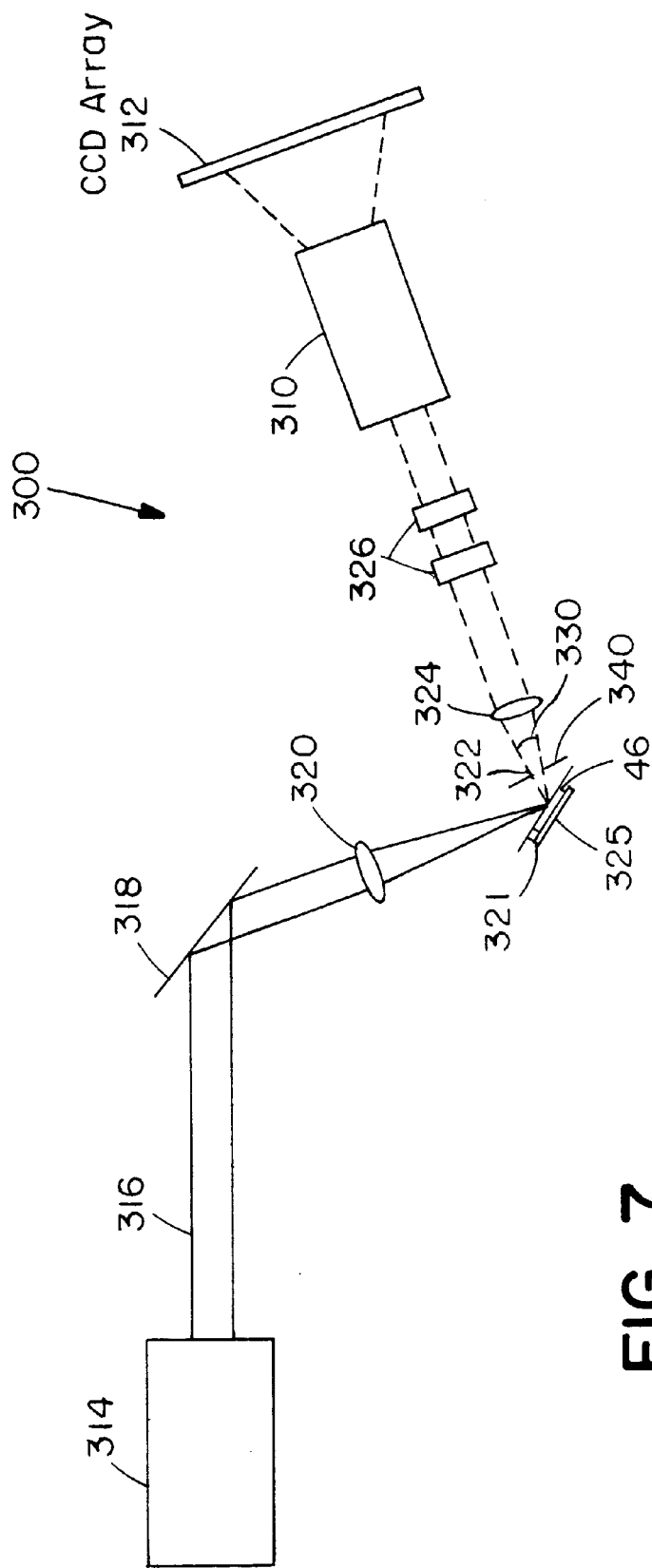
FIG. 7 is a system used for in vitro tissue analysis in accordance with the invention.

A preferred embodiment of a spectrograph system 300 employed for the collection of backscattered spectral data from excised tissue samples using a spectrograph and a charge coupled device (CCD), CMOS or other integrated solid state imaging array is illustrated in FIG. 7.

System 300 can use a broadband light source or tunable laser 314 for irradiating a sample 46. Source 314 generates a beam 316 which is directed by mirror 318 through focusing optics 320 to impinge on sample 46 mounted on a scattering substrate 325 and behind a transparent window 321. The beam was focused on the sample at an angle of incidence. The collection angle 330 can be determined by an aperture or collimator 340 and is between 2 and 12 degrees, preferably between 3 and 8 degrees.

Figure 8:
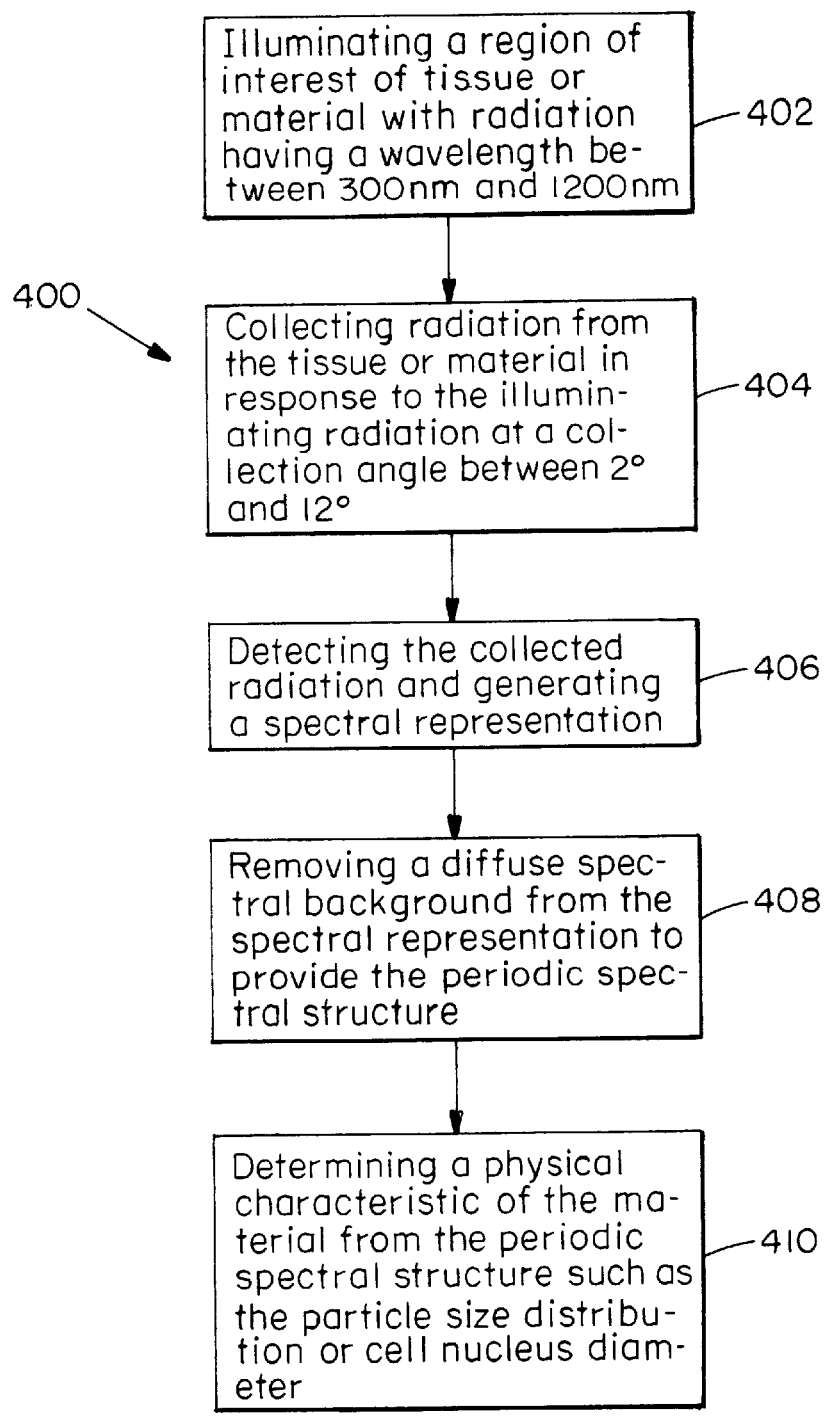
FIG. 8 is a process flow diagram illustrating a method of performing an optical diagnosis of tissue in accordance with the invention.

A portion of the scattered light 322 emitted by sample 46 was collected by collecting optics 324 a small angle relative to the incident light. In another preferred embodiment the angle of incidence and collection can be along a single common axis. Collecting optics 324 collimates and F/matches the collected light for the spectrograph 310. Prior to entering the entrance slit of the spectrograph 310, the collected light was passed through a series of filters 326 which attenuated the unwanted scattered component of the collected light. FIG. 8 illustrates generally a process 400 for collecting and analyzing the scattering spectrum from a material of interest such as tissue. The method can be performed both in vitro using a microscopy system or a color imaging system as shown in FIG. 7, or in vivo on a patient. The illuminating light 402 from a source can use radiation in the range of 300 nm–1200 nm, including the infrared range. After collecting 404 and detecting 406 radiation, the diffuse background 408 can be removed and the desired characteristics calculated 410. These results can be used to provide a diagnosis of the region of interest.

A preferred embodiment of the present invention employs an analytical method based on data collection with an optical fiber probe with fixed delivery and collection geometry. Data analysis uses light diffusion, but rather than directly apply the model to analyze tissue spectra, a correspondence is established between the diffuse reflectance spectra and a physical tissue representation composed of scatterers and absorbers with known optical properties. By analyzing spectra from this tissue model using the analytical formulation, a calibration system is provided which is simple to invert and accurately predicts the concentrations of the scatterers and absorbers. Once the calibration is established, the method is applied to tissue spectra.

The following relates to the application of spectral analysis to mucosal surfaces of tissues in vivo. In this example adenomatous colon polyps are measured, which are precursors of colon cancer. These polyps are a form of colonic dysplasia and are histologically similar to visually undetectable flat dysplasia, and are readily detectable. The results are correlated with standard histological examination, and can be used for early detection of disease and, most importantly, exemplify how this spectroscopic method can be applied in vivo to obtain morphological and biochemical information.

Diffuse reflectance spectra were collected in vivo from adenomatous polyps on 13 patients undergoing routine colonoscopy. Data were collected simultaneously with multi-excitation fluorescence spectra: a xenon-arc flashlamp with 10 µs pulse duration and an average input energy of 4Jj/pulse was used as white light source. An imaging spectrograph dispersed the collected, light and a gated diode array detector was employed for light detection in the 360–685 nm spectral range. A 12 µsec gate synchronized with the lamp pulse was used to minimize background from endoscopic illumination. The detector was controlled by a PC notebook computer, where the data were transferred and stored.

Light was delivered and collected using an optical fiber probe which was advanced through the accessory channel of the colonoscope and brought into contact with the tissue. The probe consisted of a central optical fiber for light delivery, surrounded by six concentric fibers for light collection. All fibers had 200 µm core diameter and NA=0.22. The probe tip was fitted with a quartz shield approximately 1.5 mm in length and diameter, which provided a fixed delivery/collection geometry with uniform circular delivery and collection spots in the form of overlapping cones with approximate radii of $r_d$=0.35 mm and $r_c$=0.55 mm, respectively. The tip was beveled at an angle of 17 degrees, to eliminate unwanted specular reflections from the shield/air interface.

The diffuse reflectance spectrum of a 20% by volume $BaSO_4$ powder suspension was used as a reference, to take into account the spectral characteristics and overall intensity of the xenon lamp. The probe was immersed in the suspension and a reference diffuse reflectance spectrum was recorded prior to collection of each data set. Tissue spectra were calibrated by dividing by this reference spectrum. Diffuse reflectance spectra were measured from a few different sites on every adenomatous polyp and from corresponding sites in the surrounding normal mucosa. Single-pulse excitation was used in order to avoid motional artifacts. The polyps were than removed and examined histologically, while the normal mucosa sites were not biopsied.

To represent diffuse reflectance, biological tissue was approximated as being a homogeneous semi-infinite turbid medium with reduced scattering and absorption coefficients $\mu_s'(\lambda)$ and $\mu_a'(\lambda)$, respectively ($\lambda$ is the wavelength of light). Part of the incident light is absorbed in the tissue, while the non-absorbed part is subject to multiple scattering and eventually emerges from the surface as diffuse reflectance. A certain fraction of this return light is collected by the probe, while the remaining part escapes undetected. The amount of the light collected depends on the optical properties $\mu_s'(\lambda)$ and $\mu_a'(\lambda)$, as well as on the probe diameter, $r_p$. Because $r_p$ is finite, it serves as a scale length, enabling $\mu_s'(\lambda)$ and $\mu_a'(\lambda)$ to be determined separately.

To characterize light collection by an optical probe, knowledge of the spatial and angular resolution of the diffuse reflectance on the surface of the tissue is required. Using the method of images to implement the diffusion approximation to the radiative transfer equation the diffuse reflectance radial density, $R(\lambda, r)$, at a distance r from the point of incidence of the light on the surface of a semi-infinite turbid medium is given by $$R(\lambda, r) = \frac{Z_0 \mu_s'}{4\pi \mu_s' + \mu_s} \left\{ \left(\mu + \frac{1}{r_1}\right) \frac{e^{-\mu r_1}}{r_1^2} \div \left(1 + \frac{4}{3}A\right)\left(\mu + \frac{1}{r_2}\right) \frac{e^{-\mu r_2}}{r_2^2} \right\}, \quad (6)$$

$$\text{where } \mu = (3\mu_a(\mu_a - \mu_s'))^{1/2}, \quad z_0 = \frac{1}{\mu_s' + \mu_a'}$$

$$\text{and } r_l = (z_0^2 + r^2)^{1/2}, \quad r_2 = \left(z_0^2\left(1 + \frac{2}{3}A\right)^2 + r^2\right)^{1/2}$$

The parameter A depends on the refractive index n of the medium (A=1 for n=1 and A>1 for n>1). A reasonable assumption for the average refractive index of colon tissue is n≅1.4 so that A≅3.2.

To find the total light collected by the probe, Eq. 6 must be integrated over the spatial extend of the delivery and collection areas, characterized by radii $r_d$ and $r_c$, respectively. Assuming the incident light intensity to be uniform over the entire delivery area, the diffuse reflectance $R_p(\lambda)$ collected by the probe is given by $$R_p(\lambda) = \frac{1}{r_d^2} \int_0^{r_c} r dr \int_0^{2\pi} d\Phi \int_0^{r_d} R(\lambda, \vec{r} - \vec{r}') r' dr', \quad (7)$$

$$\text{with } |\vec{r} - \vec{r}'| = (r^2 + r'^2 - 2rr'\cos\Phi)^{1/2}.$$

The integrals is Eq. 7 can be evaluated numerically. However, to obtain a simple analytical expression for $R_p(\lambda)$, we assume point delivery of light ($r_d$=0) and collection over a circular spot of radium $r_c$, we then obtain:

$$R_p(\lambda) = 2\pi \int_0^{r_c} R(r) r dr \quad (8)$$

$$= \frac{\mu_s'}{\mu_s' + \mu_a} \left\{ e^{-\mu z_0} \times e^{-(1+\frac{3}{4}A)\mu z_0} - z_0 \frac{e^{-\mu r_1'}}{r_1'} - \left(1 + \frac{4}{3}A\right) Z_0 \frac{e^{-\mu r_2'}}{r_2'} \right\}$$

$$\text{with } r_1' = (z_0^2 + r_c^2)^{1/2}, \quad r_2' = \left(z_0^2\left(1 + \frac{2}{3}A\right)^2 + r_c^2\right)^{1/2}$$

The optimal value of $r_c$ was found by calibrating Eq. 8 on physical tissue models with known optical properties. The advantage of using Eq. 8 is that it is much easier to invert than Eq. 7, which requires numerical integration. Eq. 8 gives the diffuse reflectance at the perpendicular direction to the tissue surface. This is acceptable because light is only collected by the optical probe at directions with a maximum deviation of approximately 10 degrees from the direction perpendicular to the surface.

Figure 9:
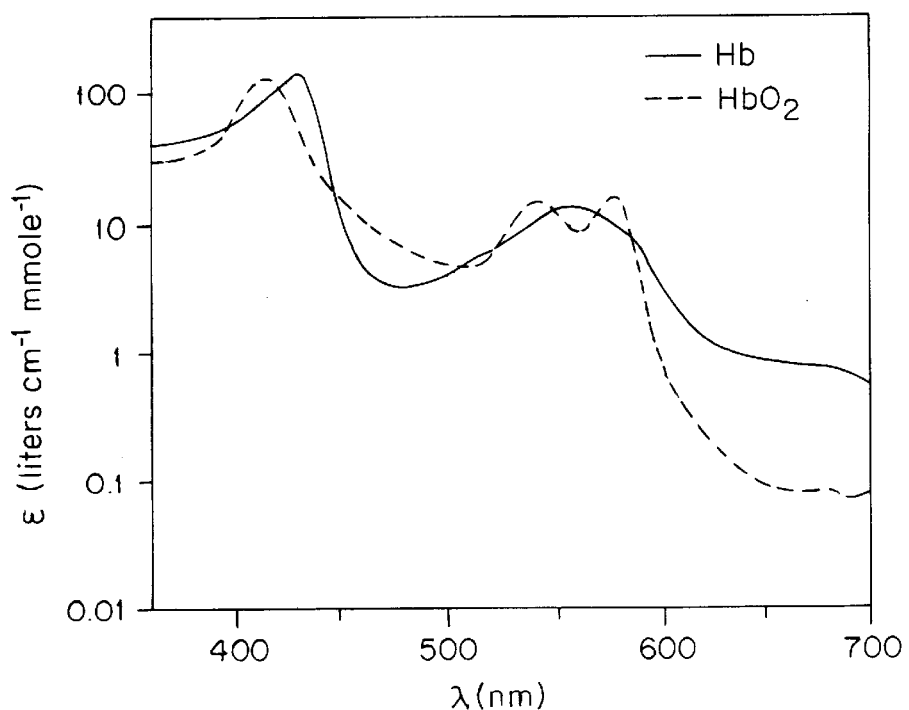
FIG. 9 is the molar extinction coefficient spectra (per heme group) of the oxygenated (thin line) and deoxygenated (thick line) hemoglobin (21). Note the characteristic peaks at 415, 542, and 577 nm (oxyhemoglobin-$HbO_2$) and at 430 and 555 nm (deoxyhemoglobin-Hb).

Eq. 8 can be used to analyze the diffuse reflectance spectra collected by the probe. From these measurements of the tissue spectra, hemoglobin is the only significant light absorber in colon tissue in the visible range of the spectrum, and is encountered in both oxygenated and deoxygenated forms. The light absorption properties of both forms have been studied and their molar extinction coefficient spectra $\varepsilon_{HbO2}(\lambda)$, $\varepsilon_{Hb}(\lambda)$ are shown in FIG. 9. oxyhemoglobin absorption presents a maximum at 415 nm and two secondary maxima at 542 and 577 nm, while deoxyhemoglobin has a maximum at 430 nm and only one secondary maximum at 555 nm. The total absorption coefficient, $\mu_j(\lambda)$ is given by $$\mu_j(\lambda) = 2.3 C_{Hb}'(\alpha \varepsilon_{HbO_2}(\lambda) + (1-\alpha)\varepsilon_{Hb}(\lambda)), \quad (9)$$

$$\text{where } \alpha = \frac{C_{HbO_2}}{C_{HbO_2} + C_{Hb}}$$

is the Hb oxygen saturation parameter, $C_{HbO2}$ and $C_{Hb}$ are the concentrations of oxy and deoxy Hb, respectively, and $C'_{Hb}=C_{HbO2}+C_{Hb}$ the total concentration of HB.

Determination of $C_{Hb}$ and α was performed in the following way. For a given tissue spectrum, $R_p(\lambda)$, initial values were assigned (typically $C_{Hb}$=0.0 and α=0.5). Eq. 8 was then numerically inverted to find $\mu_s'(\lambda)$, which exhibited residual spectral features of HB absorption. The parameters $C_{Hb}$ and α were then modified, and the process was repeated recursively until $\mu_s'(\lambda)$ exhibited a smooth spectral shape with the Hb spectral features absent. In this way, $\mu_s'(\lambda)$ was simultaneously determined with $C_{Hb}$ and α.

TABLE 2

| Model Parameter | Normal | Adenomatous Polyp |
|---|---|---|
| Total Hb Concentration $C_{Hb}$ (mg/dL) | 13.6 ± 8.8 | 72.0 ± 29.2 |
| Hb Oxygen Saturation α | 0.59 ± 0.08 | 0.63 ± 0.10 |
| Effective Scatterer Density $\rho_s$ (×10$^8$ mm$^{-3}$) | 9.2 ± 7.5 | 3.5 ± 4.0 |
| Effective Scatterer Size $d_s$ (mm) | 0.56 ± 0.18 | 0.94 ± 0.44 |

The above procedure is based on the assumption that $\mu_s'(\lambda)$ is a relatively smooth function of the wavelength $\lambda$, which analysis confirms, as will become evident from the discussion below. In general, $\mu_s'(\lambda)$ is the sum of contributions from the various tissue scatterers. Unfortunately, detailed information about these individual scatterers is not available. Therefore, $\mu_s'(\lambda)$ was written as $$\mu_s'(\lambda) = \rho_s \sigma'(\lambda),$$

with $\rho_s$ the effective scattering density and $\sigma'(\lambda)$ the effective reduced scattering cross section, i.e. the tissue scattering properties are modeled in an average way, as if tissue contained a single well-defined type of scatterer. In general, $\sigma'(\lambda)$ depends on the refractive index, shape and size of the scatterer, as well as on the refractive index of the surrounding medium. For a spherical scatterer with diameter $d_s$, $\sigma'(\lambda)$ can be calculated numerically using Mie scattering theory.

Figure 10:
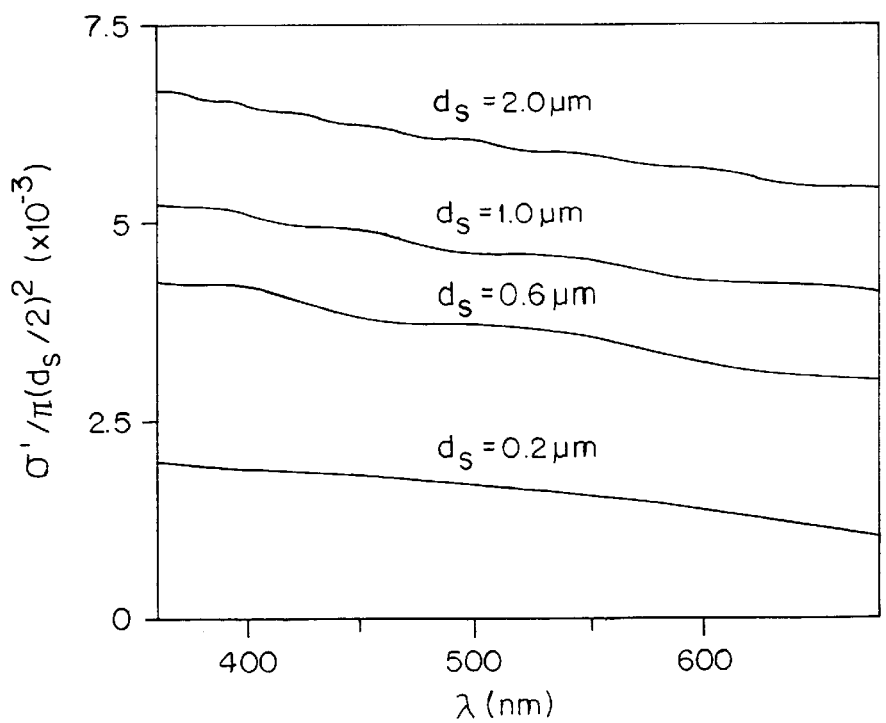
FIG. 10 is the reduced scattering cross section spectra $\sigma'$ ($\lambda$), calculated using Mie theory. Results are shown for four different diameters, $d_s$, (0.2, 0.6, 1.0, and 2.0 $\mu$m). The slope of the spectra is inversely related to the diameter. A refractive index of 1.4 was assumed for the scattering particles, and 1.36 for the surrounding medium.

FIG. 10 shows such a calculation of $\sigma'(\lambda)$. Note that the slope of $\sigma'(\lambda)$ depends on $d_s$ in a simple way i.e. the slope is inversely related to scatterer size. In this way it was possible to assign a scatterer size to every $\sigma'(\lambda)$ and hence to every $\mu_s'(\lambda)$ in the range $d_s=0.2–2.0\,\mu m$. For example, by inspecting $\mu_s'(\lambda)$ of normal colon mucosa, previously reported based on in vitro measurements, it can be seen that they correspond to a scatterer size $d_s \cong 0.35\,\mu m$. Once $d_s$ was determined, the density $p_s$ was by dividing $\mu_s'(\lambda)$ by $\sigma'(\lambda)$. In summary, for each tissue diffuse reflectance spectrum four parameters were obtained, $C_{Hb}$, $\alpha$, $p_s$ and $d_s$.

In calculating the results shown in FIG. 10, the scatterer and the surrounding medium refractive indices were assumed similar to those likely to be found in tissue. Reasonable approximations are a refractive index of approximately 1.4 for the scatterers and 1.36 for the surrounding medium. These values can be justified by noting that the lower bound for the tissue refractive index is set by the refractive index of water, which is approximately equal to 1.33 in the visible range, and the upper bound is set by the maximum refractive index reported for soft tissue, which is around 1.45. Such values are consistent with those generally observed for soft biological tissues.

The physical tissue representation served as a method for confirming the applicability of the various approximations made in developing Eq. 8. The samples consisted of mixtures of spherical microparticles with Hb in various concentrations. The model established that these mixtures simulated the optical properties of tissue samples. In addition, the range of validity of the analytical model in terms of the optical properties was established, and the optimal value for the parameter $r_c$, Eq. 8. was determined.

Polystyrene bead suspensions in de-ionized water (Polysciences, Inc.) were used to simulate tissue light scattering, and Hb solutions prepared from lyophilized human Hb (Sigma, H0267) were used to stimulate absorption. The scattering properties of the beads were calculated using Mie theory. The bead diameter was 1.07 $\mu m$, and the refractive index $n_p$ of polystyrene was given by the expression of $n_p=15607+10002/\lambda^2$ (26), ($\lambda$ in nm), and the polystyrene concentration was 0.625% by volume. The reduced scattering coefficient varied from approximately 1.7 mm$^{-1}$ at 400 nm. This spectral dependence is similar to that shown in FIG. 10 with $d_s=1.0\,\mu m$, with the difference that the slope is larger due to the larger refractive index of polystyrene.

Since light absorption by polystyrene is negligible in the visible range, absorption was solely due to oxyhemoglobin. The size of the physical-tissue model was approximately 3×3×0.5 cm, simulating the flat geometry of normal colon mucosa. Additional geometries were investigated such as a cylindrical geometry with 1 cm depth and 0.5 cm diameter, to simulate the geometry of the polyps, but no significant spectral differences were found. The range of optical parameters used was chosen based on the previously reported independent measurements of colon tissue optical parameters performed in vitro.

Figure 11:
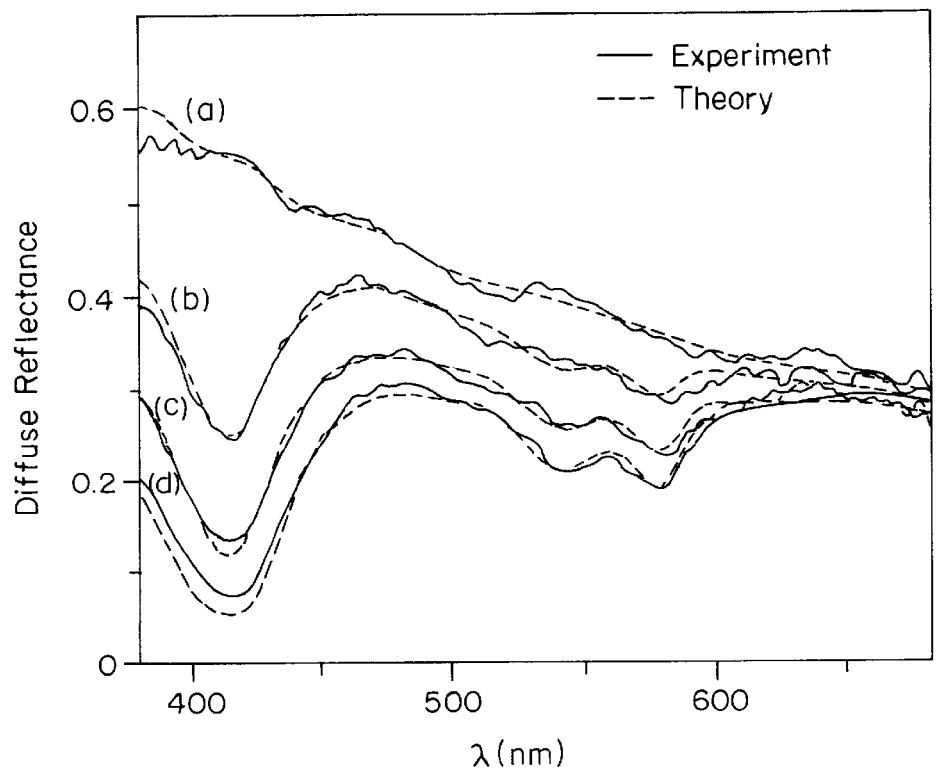
FIG. 11 shows the Diffuse reflectance spectra measured on physical tissue models (thick line) corresponding to four different Hb concentrations: (a) 0.0 mg/dL, (b) 50 mg/dL, (c) 125 mg/dL, (d) 250 mg/dL. The analytical model predictions using the same optical parameters employed in the preparation of the physical tissue models are also shown (thin line), with agreement between the analytical and the tissue model being very good.

FIG. 11 shows diffuse reflectance spectra measured on the physical tissue model with various concentrations of Hb vs. the analytical model predictions, which were obtained by setting $r_c=0.45$ mm in Eq. 3. This was determined to be the optimal value for $r_c$, which was kept fixed throughout the entire data analysis. It was also found that the parameter $Z_0=1/(0.6\,\mu_a+\mu_s')$ improved the agreement between the analytical model and the physical tissue model data, especially for large values of absorption. The physical tissue model spectra shown in FIG. 11 are very similar to the tissue spectra presented below. This fact serves as indirect confirmation of the assumptions made in developing the model, regarding tissue scatterers (modeled as microspheres) and tissue absorption (attributed to Hb).

The analytical model was found to accurately predict the physical tissue model spectra for Hb concentrations in the physiological range of interest. For Hb concentrations lower than 100 mg/dL, the deviation between the two models was always smaller than 10% over the entire wavelength range. The largest deviation occurred when absorption became comparable to scattering. This is shown in curve (d) of FIG. 11, near the peak of Hb absorption, around 415 nm. The Hb concentration was in this case 250 mg/dL which corresponds to an absorption coefficient of approximately 5 mm$^{-1}$ at 415 nm, while the scattering coefficient was approximately 2.8 mm$^{-1}$ at the same wavelength.

Figure 12:
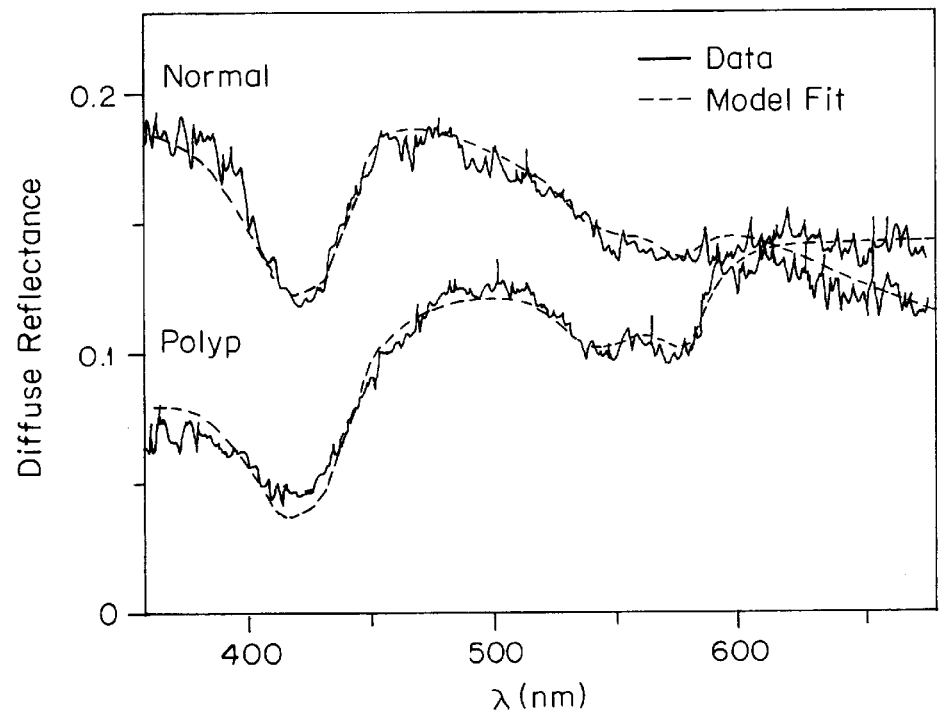
FIG. 12 shows the typical normal and adenomatous polyp spectra (thick line), and best fits to the data using the model (thin line). Mie theory was used to approximate the reduced scattering coefficient used for the model fits (see FIG. 13).

FIG. 12 shows typical diffuse reflectance spectra from one adenomatous polyp site and one normal mucosa site. Significant spectral differences are readily observable, especially in the blue region of the spectrum, where the Hb absorption valley around 420 nm is the prominent spectral feature. This valley is much more prominent int he polyp spectrum, which also shows a continuous decrease in intensity starting from the red end (~700 nm) and moving toward the green region (~500 nm) of the spectrum, while in the same range the normal mucosa spectrum shows a steady increase in intensity. The secondary absorption dips of oxyhemoglobin (542 and 577 nm) are much more prominent in the adenomatous polyp spectrum, indicating increased Hb concentration. According to the model analysis the normal mucosa spectrum was characterized by Hb concentration $C_{Hb}=22.5$ mg/dL, while the corresponding value for the adenomatous polyp was about 6 times higher ($C_{Hb}=165$ mg/dL). The Hb saturation was found to be 0.65±0.05, and 0.55±0.05 respectively.

Figure 13:
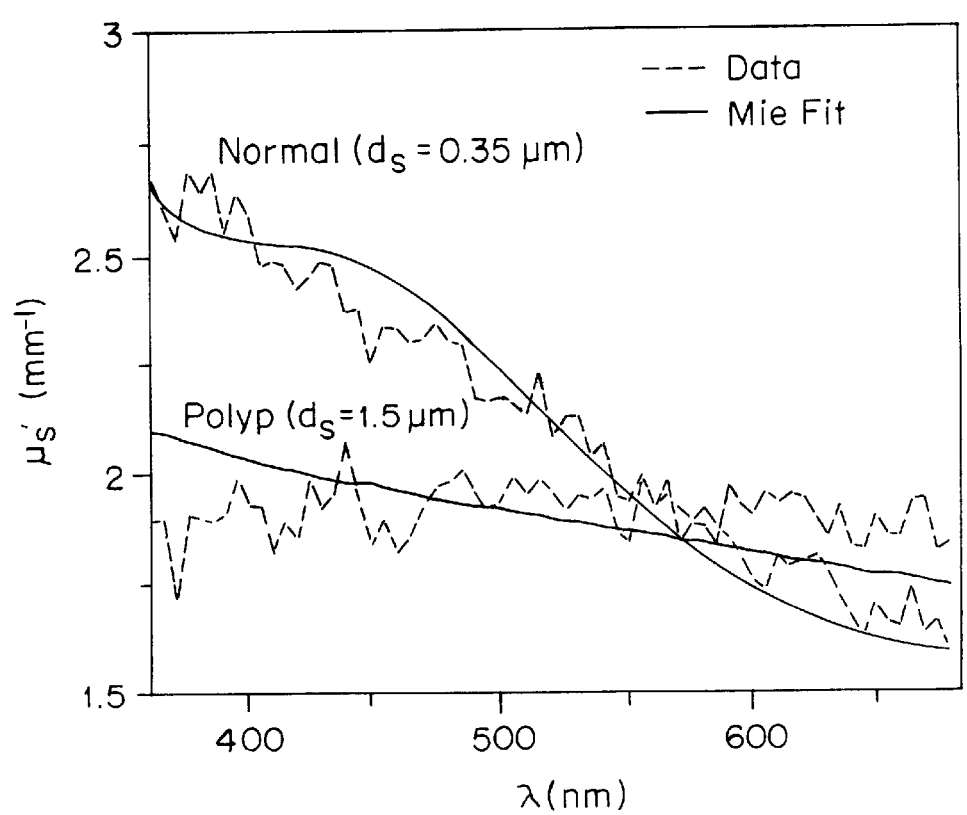
FIG. 13 shows the scattering spectra obtained from the data shown in FIG. 12 (thin line), and best fits using Mie theory (thick line). The Mie theory fits assign an effective scatterer size $d_s$ to the reduced scattering spectra. The polyp is characterized by a larger effective scatterer size ($d_s$=1.5 $\mu$m) as compared to normal mucosa ($d_s$=0.35 $\mu$m)
Figures 14A, 14B:
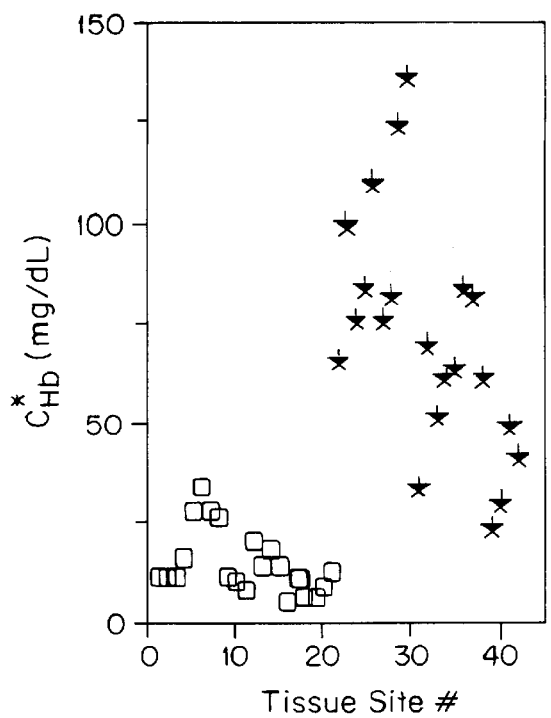
FIG. 14A–14D show parameters obtained from data analysis: (A) total Hb concentration. $C_{Hb}$, (B) Hb oxygen saturation, $\alpha$ (C) effective scatterer density, $p_s$, and (D) effective scatterer size, $d_s$. The largest difference between normal mucosa (squares) and adenomatous polyps (stars) is observed in the total Hb concentration.
Figure 14C:
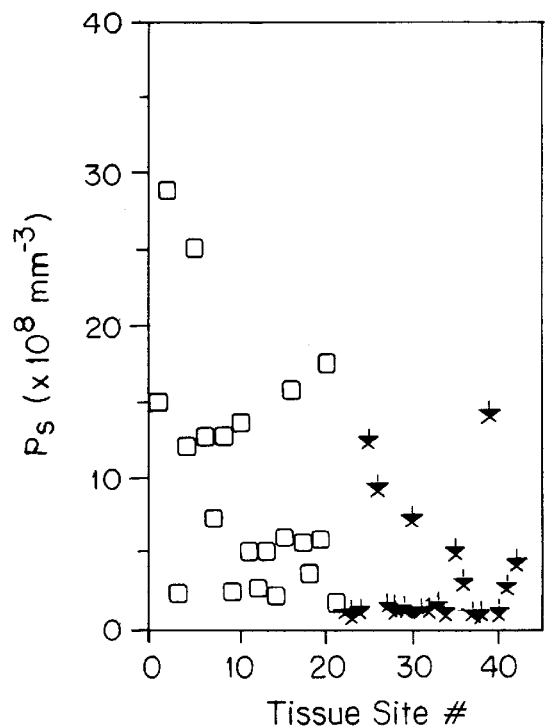
Figure 14D:
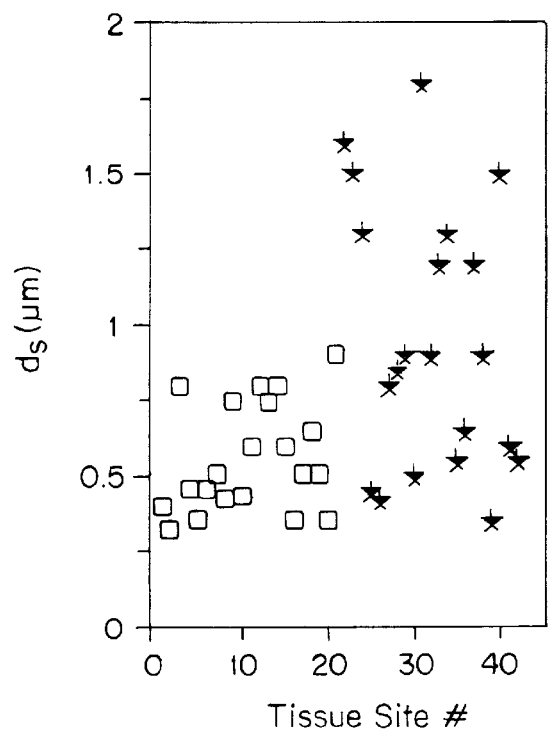

FIG. 13 shows the scattering spectra $\mu_s'(\lambda)$ calculated from the data shown in FIG. 12, along with the best Mie theory fits. The main difference between the spectra of the two tissue types is observed in the spectral slope, which corresponds to different effective scattering sizes, $d_s=1.5\,\mu m$ for the polyp and $d_s=0.35\,\mu m$ for normal mucosa. The values for the scatterer densities were found to be $p_s=15 \times 10^8$ mm$^{-3}$ for the normal mucosa, and $p_s=1.3 \times 10^8$ mm$^{-3}$ for the adenomatous polyp. FIG. 12 also shows the best analytical model fits to the data, using Eq. 8. The model accurately describes the data, despite the dramatic differences noted in the spectral shape between the two tissue types and the fact that $\mu_s'(\lambda)$ is approximated assuming a homogeneous distribution of spherical scatterers. The deviation between the data and the model in typically smaller than 10% for most of the wavelength range.

FIGS. 14A–14D shows the calculated values of the four parameters for all tissue sites studied: (A) total Hb concentration $C_{Hb}$ (B) Hb oxygen saturation $\alpha$, (C) effective scatterer density $p_s$ and (D) effectiveness scatterer size $d_s$. Adenomatous polyps were clearly characterized by increased Hb concentration, while there were no observable differences in terms of the Hb oxygen saturation. The effective scatterer density was in general lower in adenomatous polyps, and the effective scatterer size larger, even though there was significant overlap of these parameter distributions between the two tissue types. Table 2 summarizes the results shown in FIGS. 14A–14D by giving the average values and the standard deviations for each parameter.

Figure 15:
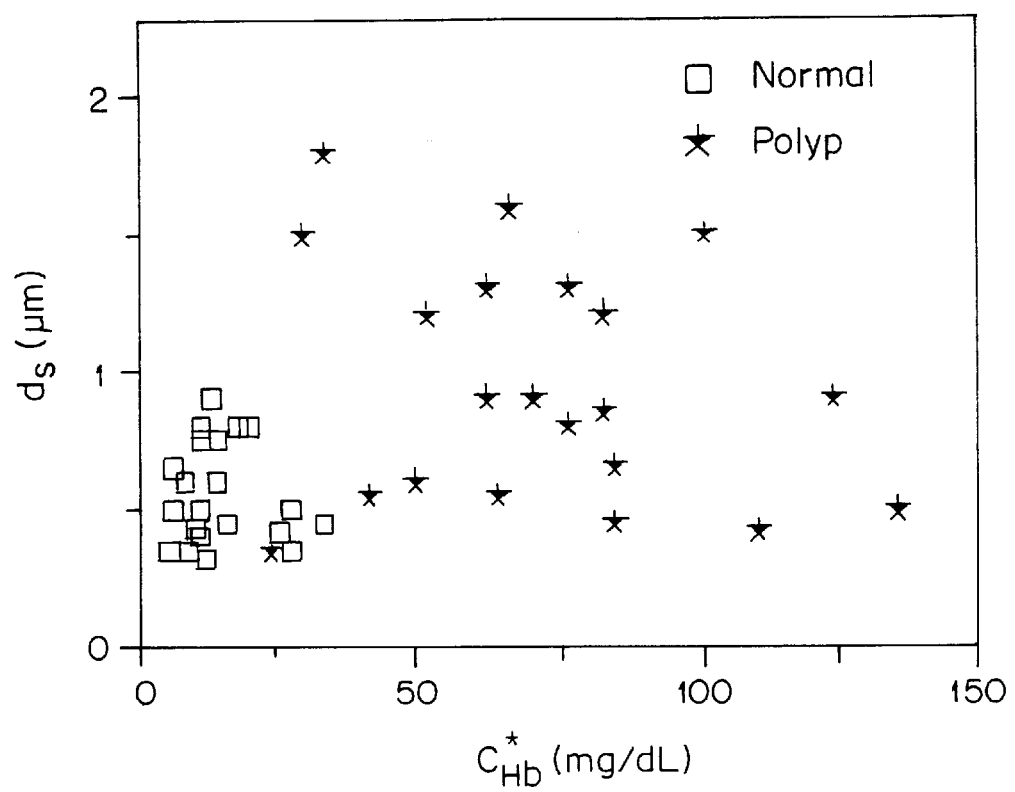
FIG. 15 is a binary plot of the total Hb concentration $C_{Hb}$ vs. the effective scatterer size $d_s$. The normal data tend to form a well defined cluster, while the adenomatous polyp data are marked by wider variation.

FIG. 15 shows a plot of the Hb concentration $C_{Hb}$, vs. the effective scatterer size $d_s$. These two parameters are shown together in order to summarize and illustrate the differences found in the scattering and absorption properties of normal mucosa and adenomatous polyps in the colon. Note that the normal mucosa data tend to form a cluster, while the adenomatous polyp data are separated, and characterized by a wider spread and irregular distribution, in both the effective scatterer size and the Hb concentration.

A methodology has been described which provides quantitative information about colon mucosal tissues in vivo, based on diffuse reflectance measurements. The main components of this methodology are (a) data collection through an optical fiber probe with a fixed delivery/collection geometry, (b) an analytical model for data analysis based on light diffusion, and (c) a physical tissue model for calibration of the analytical model.

The use of an optical probe with fixed geometry enables consistent data collection, and independent determination of the scattering and absorption. Modeling of the probe geometry is facilitated through the use of the parameter $r_c$, which also defined the probe's sensitivity to absorption. A probe with large $r_c$ will render the spectra collected more sensitive to tissue absorption as compared to a probe with a smaller $r_c$. In FIG. 4, the secondary Hb absorption peaks are barely noticeable in the normal mucosa spectrum: a probe with larger $r_c$ would make these features more prominent.

The analytical diffusion theory model is amenable to numerical inversion and successfully describes the tissue data after calibration on the physical tissuemodel composed of polystyrene beads and oxy hemoglobin. Other researchers have already used variants of the analytical model described here, in the study of diffuse reflectance from tissues and physical tissue models in the IR range. The present study is, to our knowledge, the first to apply the model in the visible range, to in vivo data from human mucosal tissue, measured with an optical fiber probe. By working in the visible rather than in the IR, light penetration was restricted to approximately 0.5 mm, i.e. the mucosa layer where precancerous changes occur. Using the model, we have shown that it is possible to obtain quantitative information about the tissue studied, such as Hb concentration, Hb oxygen saturation, effective scatterer size, and effective scatterer density. The results show that diffuse reflectance provides a tool for quantitative analysis of mucosal tissue surfaces in vivo.

The basic approximation made in the model is that Hb is the only significant absorber in colon mucosa in the visible range of the spectrum. Even though this assumption lacks direct confirmation, the fact that the data strongly exhibit the characteristic features of Hb absorption, clearly indicates that Hb is a major absorber. In addition, the spectra measured on the tissue physical model, in which Hb was the only absorber, closely resemble the tissue spectra.

In a similar way, tissue scattering was modeled as due to homogeneous spherical scatterers with known refractive index. The approximation permits a quantitative characterization in terms of two basic parameters, the effective scatterer size and the effective scatterer density. These parameters provide an estimate of the average scattering properties. The fact that the spectra measured on physical tissue models reproduce the actual tissue spectra, serves again (as in the case of Hb), as an indirect confirmation of the validity of this approximation.

Data analysis showed that adenomatous colon polyps were characterized by increased Hb concentration. It is known that tumors and cancerous tissues exhibit increased microvasculature, and hence increased blood content. Using morphometry and vascular casting in combination with scanning electron microscopy techniques. Precancerous tissues such as adenomatous polyps of the colon are also characterized by increased microvascular volume the above in agreement with these reports in terms of observing the increased Hb concentration. Others report increased microvascularity of the colon mucosa associated with Crohn's disease and ulcerative colitis. Even though we did not study these tissue types, the technique employed here could prove useful for the in vivo study of such diseases.

The Hb oxygen saturation was found to be approximately 60%, on average, for both normal mucosa and adenomatous polyps. This result is reasonable, because the measurements were essentially performed in the capillary network of the mucosa, where oxygen is transferred from Hb to tissue. Hb oxygen saturation drops within the capillaries from approximately 97% (arterial blood) to about 40% (venous blood) with the measured values (around 60–70%) appropriately placed int he middle of this range. The fact that there were no differences observed between the two tissue types, can probably be attributed to the fact that adenomatous polyp metabolism is not significantly altered, so as to introduce changes in Hb oxygenation, which is probably related to the disturbed metabolism of such tissues. The technique presented here could be used in vivo for the study of tumors on the surfaces of hollow organs, or for the study of other tissue types when knowledge of Hb saturation is needed.

An intrinsic differentiation in the scattering properties between the two tissue types was observed. For adenomatous polyps, the average effective scattering size was larger, and the average effective scatterer density was smaller, as compared to normal mucosa. There are a number of hypotheses identifying contributions to scattering from various microstructures, both extracellular such as collagen fibers, and intracellular such as mitochondria and cell nuclei. One model provides contributions to light scattering from intracellular structures is increased in adenomatous polyps because cells occupy a higher volume ratio. In addition, the submucosa, in which collagen is more densely packed is usually located too far away from the polyp surface in order to be able to contribute to light scattering. This can explain the lower scatterer density in adenomatous polyps, provided that intracellular scatterers are larger than extracellular ones, on average.

EQIVALENTS

While this invention has been particularly shown and described with reference to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of endoscopically measuring a size of a structure in a layer of tissue comprising:
   directing radiation having a plurality of wavelengths in a range between 350 nm and 700 nm through an endoscope onto a region of interest in the layer of tissue;
   collecting radiation from the tissue;
   detecting the collected radiation to provide a detected spectrum; and determining a size of a structure within the tissue layer from the detected spectrum.

2. The method of claim 1 further comprising determining if the region of interest includes dysplastic tissue.

3. The method of claim 1 further comprising directing radiation onto the tissue using a fiber optic probe.

4. The method of claim 1 further comprising collecting the radiation from the tissue with a fiber optic probe.

5. The method of claim 1 further comprising determining an average nuclear size of nuclei within the region of interest.

6. The method of claim 1 further comprising measuring a diameter of a tissue nucleus within the region of interest.

7. The method of claim 1 further comprising measuring a periodic component of the detected spectrum as a function of wavelength.

8. The method of claim 7 further comprising determining the size of a nucleus in the tissue from the periodic component.

9. A method of optically measuring a physical characteristic of tissue comprising:

A directing radiation having a plurality of wavelengths in a range between 350 nm and 700 nm through an endoscope onto a region of interest in tissue to be measured;

collecting radiation from the tissue; and measuring a periodic component of collected radiation as a function of wavelength to determine a physical characteristic of the tissue.

10. The method of claim 9 further comprising determining if the region of interest includes dysplastic tissue.

11. The method of claim 9 further comprising directing radiation onto the tissue using a fiber optic probe.

12. The method of claim 9 further comprising collecting the radiation from the tissue with a fiber optic probe.

13. The method of claim 9 further comprising determining an average nuclear size of nuclei within the region of interest.

14. The method of claim 9 further comprising measuring a diameter of a tissue nucleus within the region of interest.

15. The method of claim 9 further comprising collecting radiation with the endoscope, the endoscope having an imaging sensor at a distal end of the endoscope.

16. The method of claim 9 further comprising determining a density of nuclei in the tissue from the periodic component.

17. A method of determining a presence of dysplasia in tissue comprising:

directing radiation having a plurality of wavelengths in a range between 350 nm and 700 nm through an endoscope onto a region of interest in an epithelial layer of tissue such that radiation is backscattered by the tissue;

collecting the backscattered radiation from the tissue;

detecting the collected backscattered radiation with a detector to provide a scattering spectrum; and determining the presence of dysplasia in the region of interest of the tissue with the scattering spectrum.

18. The method of claim 17 further comprising determining if the region of interest includes dysplastic tissue.

19. The method of claim 17 further comprising collecting radiation in the range of 350 nm to 700 nm.

20. The method of claim 17 further comprising collecting the radiation from the tissue with a fiber optic probe.

21. The method of claim 17 further comprising determining an average nuclear size of nuclei within the region of interest.

22. The method of claim 17 further comprising measuring a diameter of a tissue nucleus within the region of interest.

23. The method of claim 17 further comprising measuring a periodic component of the scattering spectrum as a function of wavelength.

24. The method of claim 17 further comprising determining the size of a nucleus in the tissue from the periodic component.

25. A method of optically measuring a physical characteristic of a material comprising:

directing radiation having a plurality of wavelenths in a range between 350 nm and 700 nm through an endoscope onto a region of interest in the material tissue to be measured;

collecting radiation from the material;

detecting a scattering spectrum from the collected radiation; and measuring a periodic component from the scattering spectrum as a function of wavelength to determine a physical characteristic of the material.

26. The method of claim 25 further comprising directing radiation onto the material using a fiber optic probe.

27. The method of claim 25 further comprising collecting the radiation from the material with a fiber optic probe, the probe having an optical fiber with a numerical aperture in a range of 0.05–0.25.

28. The method of claim 25 further comprising determining an average nuclear size of nuclei within the region of interest.

29. The method of claim 25 further comprising measuring a number of particles per unit area within the region of interest.

30. An endoscope apparatus for optically measuring a physical characteristic of tissue comprising:

a radiation source that illuminates a region of interest in tissue to be measured through an endoscope with radiation having a plurality of wavelengths in a range between 350 nm and 700 nm;

an optical system in the endoscope that collects radiation from the tissue;

a detector system that senses the collected radiation; and a data processor that determines a periodic component of detected radiation as a function of wavelength to determine a physical characteristic of the tissue.

31. The apparatus of claim 30 wherein the radiation source comprises a broadband light source.

32. The apparatus of claim 30 further comprising a fiber optic probe that couples the source to the tissue.

33. The apparatus of claim 30 further comprising a fiber optic probe that collects the light in a collection angle between 2 and 12 degrees.

34. The apparatus of claim 33 wherein the fiber optic probe is insertable in an endoscope.

* * * * *